United States Patent [19]

Wolcott et al.

[11] Patent Number: 5,346,605
[45] Date of Patent: Sep. 13, 1994

[54] APPARATUS FOR QUANTITATIVE DETERMINATION OF CHEMICAL OXIDIZING OR REDUCING AGENTS IN A FLUID ENVIRONMENT

[75] Inventors: Duane K. Wolcott, Baton Rouge; Stephen A. Noding, Brusly, both of La.

[73] Assignee: The Dow Chemical Company, Midland, Mich.

[21] Appl. No.: 84,786

[22] Filed: Jun. 29, 1993

Related U.S. Application Data

[63] Continuation-in-part of Ser. No. 934,203, Aug. 24, 1992, abandoned.

[51] Int. Cl.$^5$ .................. G01N 27/40; G01N 27/404
[52] U.S. Cl. .................. 204/412; 204/153.13; 204/415; 204/431; 204/432
[58] Field of Search .................. 204/153.13, 183.17, 204/412, 415, 431, 432, 414, 430

[56] References Cited

U.S. PATENT DOCUMENTS

| | | | |
|---|---|---|---|
| 2,850,640 | 9/1958 | Dudley et al. | 250/43.5 |
| 3,474,661 | 10/1969 | Gerdes et al. | 73/27 |
| 3,712,860 | 1/1973 | Gabrusenok | 204/430 |
| 3,713,994 | 1/1973 | Shults et al. | 204/413 |
| 3,761,377 | 9/1973 | Mang | 204/153.13 |
| 3,824,171 | 7/1974 | Van Houwelingen et al. | 204/419 |
| 3,902,982 | 9/1975 | Nakagawa | 204/212 |
| 3,996,123 | 12/1976 | Kruishoop | 204/153.1 |
| 4,172,770 | 10/1979 | Semersky et al. | 204/415 |
| 4,176,215 | 11/1979 | Molnar et al. | 521/27 |
| 4,269,685 | 5/1981 | Parker | 204/414 |
| 4,333,810 | 6/1982 | Wolcott et al. | 204/153.13 |
| 4,460,448 | 7/1984 | Wolcott | 204/266 |
| 4,689,135 | 8/1987 | Lungu et al. | 204/415 |
| 4,724,050 | 2/1988 | Bergeron et al. | 204/131 |
| 4,894,138 | 1/1990 | Gambert | 204/415 |

*Primary Examiner*—T. Tung

[57] ABSTRACT

An apparatus for the quantitative determination of chlorine in a fluid environment, comprising a flat ion exchange membrane-based sensor which utilizes a layer of an electrochemically inert hydrated salt or combination of such salts to provide water for the reduction of such chlorine to chloride ion, and the detection of chlorine by such reduction.

23 Claims, 2 Drawing Sheets

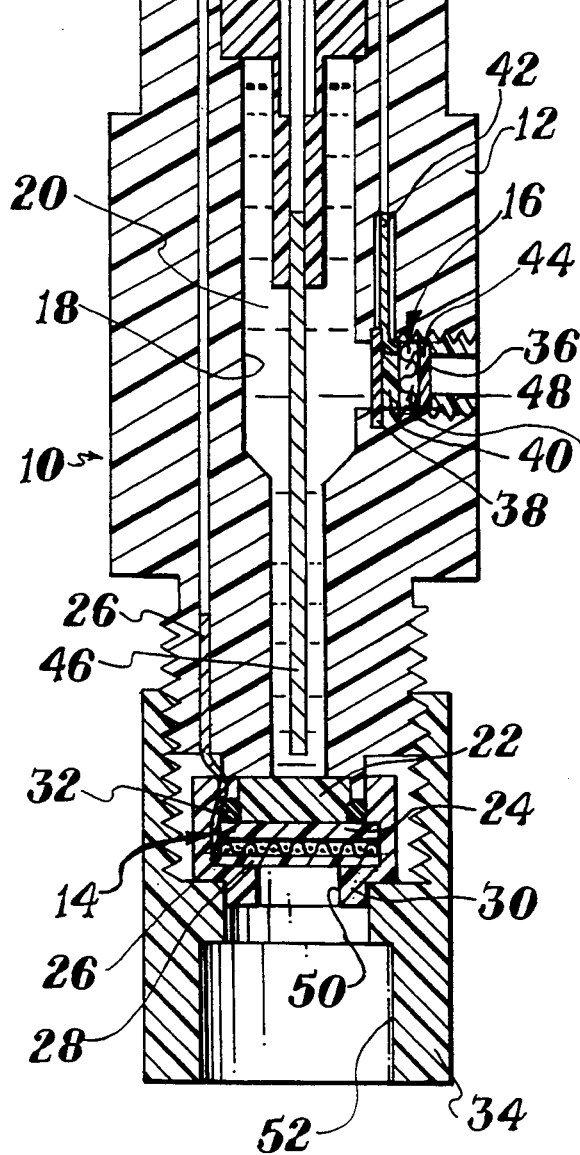
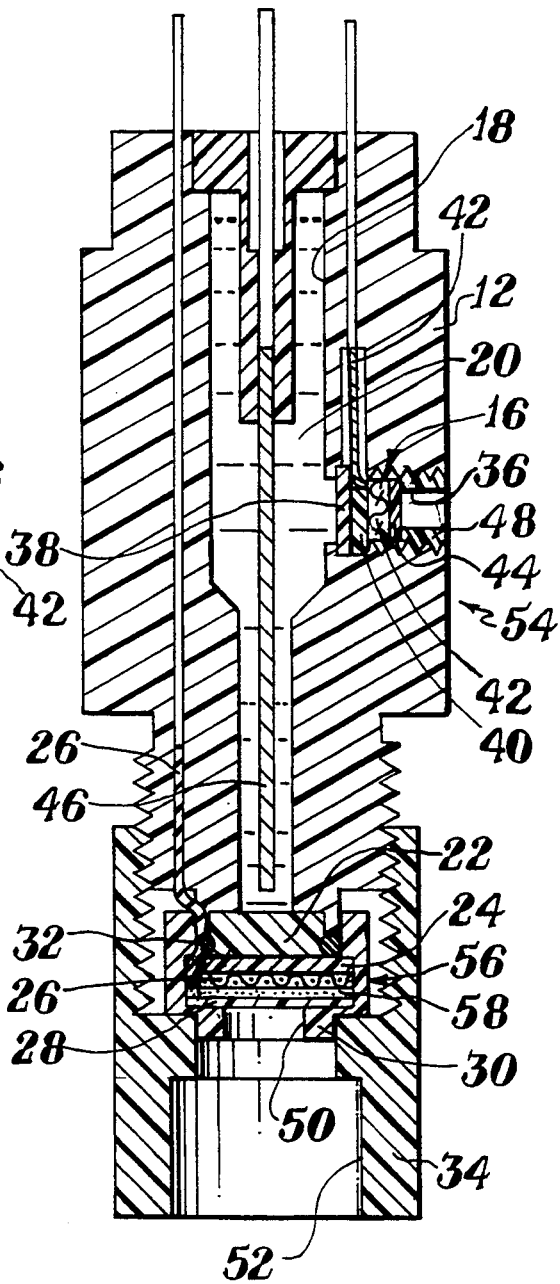

APPARATUS FOR QUANTITATIVE DETERMINATION OF CHEMICAL OXIDIZING OR REDUCING AGENTS IN A FLUID ENVIRONMENT

CROSS-REFERENCE TO RELATED APPLICATION

This is a continuation-in-part of application Ser. No. 07/934,203, filed Aug. 24, 1992, now abandoned.

BACKGROUND OF THE INVENTION

This invention relates to the quantitative determination of chemical oxidizing and reducing agents in a fluid (gas or liquid) environment. More particularly, the invention relates to the determination of chemical oxidizing and reducing agents by means of a sensor or detector apparatus employing an ion-exchange membrane.

A sensor apparatus of this type is disclosed in commonly-assigned U.S. Pat. No. 4,333,810 to Wolcott et al. (the '810 patent), wherein a tubular ion-exchange membrane is employed to contain an electrolyte solution, and to separate a first electrode in contact with its fluid environment and wrapped around the membrane and a second electrode positioned in the electrolyte solution. Means are provided for measuring a flow of electrical current between the first and second electrodes attributable to the oxidizing or reducing agents coming into contact with the first electrode, for example, a microammeter or resistor in parallel combination with a voltmeter. An additional means for imposing a voltage across the electrodes is provided in certain embodiments, e.g., a battery or an alternating power source stepped down with a direct current transformer or rectifier, and a chart recorder or the like may be employed in conjunction with the current measuring means.

A second membrane-based, galvanic-type sensor apparatus known to us employs a flat membrane for containing an electrolyte solution and for separating a first electrode in contact with the fluid environment and a second electrode in the electrolyte solution. The first electrode in this flat-membrane design is in the form of a flat wire mesh, and the remainder of the apparatus apart from the sensor proper may be as described in the '810 patent.

An amperometric variation of this second, flat-membrane design employs a third, driven electrode to supply the current that would otherwise be supplied by the corrosion of the second or reference electrode, whereby the effective lifetime of the second electrode may be substantially extended. This three-electrode, flat-membrane sensor apparatus is depicted in FIG. 1, and its construction and manner of operation will be described in detail below.

As discussed in the '810 patent, the art prior to the '810 patent had the electrodes forming a part of the electrochemical cell in the sensors separated from each other by a porous layer. This porous layer design, however, permitted a substantial diffusion of a sample throughout the electrolyte between the electrodes, so that particularly after exposure to a high concentration of the particular oxidizing or reducing agent in question a long recovery time was required to stabilize the sensor and to again enable the detection of lower concentrations. The porous layer was also non-selective, and allowed interfering or poisonous species to pass freely into contact with the electrodes.

The sensor apparatus in the '810 patent and the two- and three-wire flat membrane sensor apparatus described above don't have the lengthy recovery and contamination problems associated with the previous electrochemical sensors, but have not overcome another significant problem with the known sensor apparatus of oxidizing and reducing agents such as chlorine. Typically these sensor apparatus detect chlorine through the reduction half-reaction of chlorine, and water participates in this reduction.

As a consequence of this participation, all of the previously known chlorine sensors have a degree of sensitivity to fluctuations in the water content of the sensor's immediate environment. One significant use of chlorine sensors is as perimeter monitors for atmospheric chlorine. In those climates which are characterized by cold, dry winter climates for example, the known chlorine sensors have largely been rendered ineffective. For the same reasons, chlorine sensors have heretofore not proven useful as process monitors in the monitoring of anhydrous or low water-content process streams.

SUMMARY OF THE INVENTION

The present invention provides a new and improved apparatus for the quantitative determination of chemical oxidizing or reducing agents in a fluid environment, and especially in a gaseous environment, which in one aspect is substantially insensitive to changes in the water content of the fluid environment, and which in a second aspect is effective even in anhydrous or low water-content fluid environments.

The sensor portion of the apparatus in one embodiment includes:

a first, sensing electrode for contacting oxidizing or reducing agents in the fluid environment;

a layer of an electrochemically inert hydrated salt or salts positioned adjacent the first electrode and through which an oxidizing or reducing agent species must pass to encounter the first electrode;

means for retaining the layer of salt(s) in such position;

a reservoir of an electrolytic solution;

a second, reference electrode in contact with the reservoir of electrolytic solution; and an ion-exchange membrane separating the electrolytic solution and second electrode from the first electrode. The first and second electrodes in a completed apparatus are placed in electrical contact, and means are provided for measuring a flow of electrical current generated between the electrodes.

In a second, more preferred embodiment the sensor portion includes:

a first, sensing electrode for contacting oxidizing or reducing agents in the fluid environment;

a reservoir of an electrolytic solution;

a second, reference electrode in contact with the reservoir of electrolytic solution;

a layer of an electrochemically inert hydrated salt or salts positioned adjacent the first electrode and through which an oxidizing or reducing agent species must pass to encounter the first electrode;

means for retaining the layer of salt(s) in such position;

a third, externally-driven electrode which in operation is in contact with the fluid environment and which supplies current to the sensing electrode that would otherwise be supplied by the corrosion in the electrolytic solution of the second electrode;

a first ion-exchange membrane separating the electrolytic solution and second electrode from the first electrode; and a second ion-exchange membrane separating the electrolytic solution and second electrode from the third electrode.

Whereas previous sensors have relied upon atmospheric or environmental water to take part, for example, in the reduction of chlorine, the apparatus of the present invention (in either embodiment) employs the water held in the layer of hydrated salt or hydrated salts. The salt is thereafter rehydrated from the fluid environment, or if the fluid environment does not contain sufficient water to rehydrate the salt, then water from the electrolytic solution diffuses through the ion-exchange membrane to maintain an equilibrium. A steady and ample supply of water is in this fashion continuously made available for participating in the reduction of chlorine, whereby a quantitative determination of chlorine's concentration in the fluid environment may be had.

BRIEF DESCRIPTION OF THE DRAWINGS

FIG. 1 is a cross-sectional view of the sensor portion of a sensor apparatus of the three-wire, flat-membrane variety which is known to us and to which reference is made above.

FIG. 2 is a cross-sectional view of the sensor portion of a sensor apparatus of the present invention.

DETAILED DESCRIPTION OF THE PREFERRED EMBODIMENTS

Figure 3:
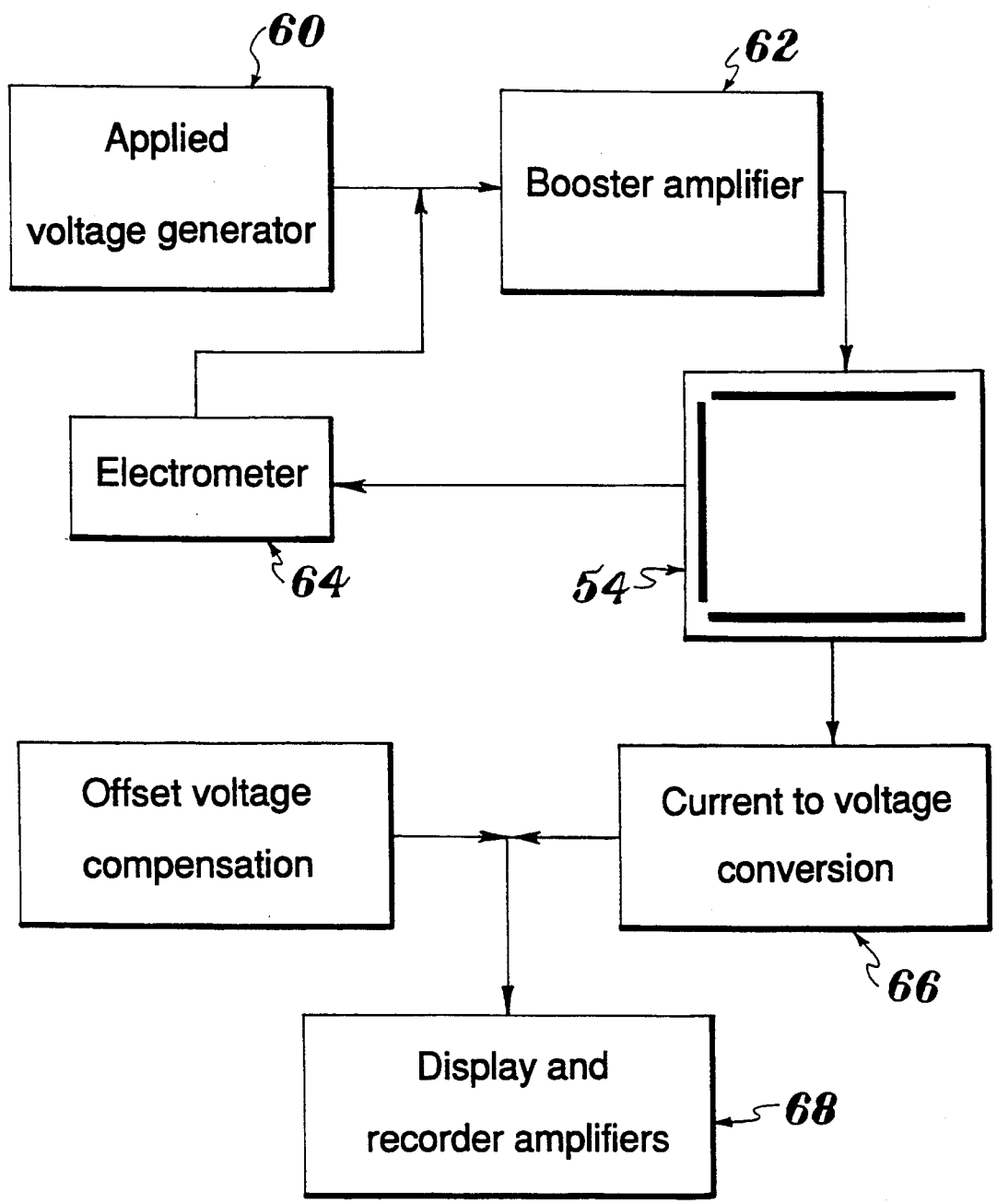
FIG. 3 is a schematic illustration of the electronic elements of the inventive sensor apparatus of FIG. 2.

The present invention in its preferred embodiments can most readily be understood by a detailed description of a certain sensor apparatus known to us and of the improvements made to this basic apparatus by the present invention. Accordingly, referring now to the drawings and more particularly to FIG. 1, a membrane-based, amperometric sensor apparatus known to us comprises a sensor 10, a sensing or measuring means (not shown) for measuring the concentration of an oxidizing or reducing agent species in a fluid environment into which the sensor 10 is placed, and means (also not shown in FIG. 1) for feeding a flow of current back to the sensor 10 to reduce the load on the reference electrode used in the sensor 10.

The sensor 10 shown in cross-section in FIG. 1 comprises a hollow and generally cylindrical sensor body 12 which, with a first flat ion-exchange membrane assembly 14 and a second flat ion-exchange membrane assembly 16, defines a reservoir 18 of an electrolytic solution 20.

Flat ion-exchange membrane assembly 14 comprises a porous support element 22 which wets out with the electrolytic solution 20 and which provides a flat-surfaced structure for joining a flat ion-exchange membrane 24 to the sensor body 12, the flat ion-exchange membrane 24, a first, sensing electrode 26 in the form of a flat wire mesh which is positioned against the membrane 24 opposite the support element 22, and a protective semipermeable, hydrophobic Teflon TM PTFE (polytetrafluoroethylene) film layer 28 over the electrode 26.

Flat ion-exchange membrane assembly 14 is held sealingly against the sensor body 12 through a generally cylindrical element 30 which surrounds the assembly at its circumference and through an 0-ring 32 positioned at the circumference of support element 22 and between the ion-exchange membrane 24 and the sensor body 12. Element 30 is in turn compressed at its circumference by a corresponding generally cylindrical threaded element 34, with threaded element 34 being threadedly joined to the sensor body 14.

The second flat ion-exchange membrane assembly 16 is positioned in an opening 36 in the side of the cylindrical sensor body 12, and comprises a porous support element 38 which performs the same functions as the support element 22, an ion-exchange membrane 40 of the opposite variety to the membrane 24 (so that where the membrane 24 is a cation exchange membrane, the membrane 40 is an anion exchange membrane and viceversa), a third, driven electrode 42 in the form of a flat wire mesh positioned against the membrane 40, and a protective semipermeable, hydrophobic Teflon TM PTFE film layer 44 over the electrode 42. A second, reference electrode 46 is positioned in the reservoir 18 of electrolytic solution 20.

The second flat ion-exchange membrane assembly 16 is held together in a similar fashion to the first flat ion-exchange membrane assembly 14. The support element 38 spans the opening 36, and thus provides a stop against which the remaining elements of the assembly 16 are pressed. The film layer 44, third, flat wire mesh electrode 42 and membrane 40 are held firmly against the support element 38 through the threaded engagement of an annular plug member 48 and the sensor body 12 at opening 36, with the plug member 48 defining a shoulder therein for receiving the Teflon TM film layer 44 in compression at the film layer's perimeter.

The sensor body 12 is comprised of an electrically insulative material which is suited to its environment and intended use for providing structural integrity to the sensor 10, and elements 30 and 34 will preferably be made of the same material. Polyvinyl chloride (PVC) is a suitable material, for example, when the apparatus is to be used as a perimeter monitor for chlorine, for example, while the use of the apparatus as a process monitor may require different materials.

The element 30, which functions with element 34 to hold the first, flat ion-exchange membrane assembly 14 together, defines one large hole 50 (for purposes of the present inventive embodiments this single large hole 50 will be resolved into preferably many smaller holes) therein which permits an oxidizing or reducing agent species to be communicated from the fluid environment around the sensor body 12 through the central opening 52 of the generally cylindrical threaded element 34, through the semipermeable film layer 28 and thereafter to the first, sensing electrode 26 which catalytically oxidizes or reduces the species in question.

At the same time, element 34 is sufficiently long and the sensor 10 positioned so that the membrane assembly 14 is protected from potentially damaging aspects of the sensor's fluid environment. For example, where the sensor 10 is used as an atmospheric monitor for chlorine, the element 34 helps to protect the membrane assembly 14 from rain, dust and airborne dirt, sand or other particulates.

In a typical application of the sensor apparatus, the first, sensing electrode 26 is a platinum electrode and reduces chlorine to chloride ion. Chlorine and water vapor from the fluid environment are passed through the central opening 52 and hole 50 of elements 34 and 30, respectively, and then are passed through the generally thin film layer 28. The film layer 28 acts to further protect the remainder of the sensor 10 from airborne particulates, and by virtue of its hydrophobic character prevents a water barrier from rain, for example, from forming over the membrane assembly 14 while at the same time serving to retain water from the reservoir 18 of electrolytic solution 20 in the sensor body 12.

The cation exchange membrane 24 carried on porous support element 22 (the porous support element 22 typically being in the nature of a glass frit or being made from a suitably porous/electrolyte-wettable polymeric material, such as a poly(vinylidene fluoride)) prevents the chloride ions from passing into and contaminating the electrolytic solution 20. Exemplary cation exchange membranes include those sold as Nafion TM brand perfluorosulfonic acid cation-exchange membranes (E.I. DuPont de Nemours & Co., Inc.).

Leakage of the electrolytic solution 20 is substantially prevented from occurring through the porous support element 22 and around the membrane 24 and/or element 30 by the compressible 0-ring 32. The electrolytic solution 20 conventionally has been a saturated aqueous solution of lithium chloride, for example, in water, but for present purposes is preferably a gel of lithium chloride and water (the higher viscosity gel being less prone to leaking out of the reservoir 18). An electrolytic gel which has been found suitable is commercially available as "EpH" gel from Innovative Sensors, Inc., Anaheim, Calif.

The second, reference electrode 46 in the reservoir 18 of electrolytic solution 20 typically is a silver electrode, and would ordinarily be quickly consumed in the presence of significant chlorine concentrations but for the use of the third, driven electrode 42 which is typically also a platinum electrode.

This third electrode 42 oxidizes chloride ions from electrolyte 20 to compensate for the migration of lithium ions from the electrolyte 20 across membrane 24 when chlorine is reduced to chloride ions at the electrode 26, and with associated means for doing so feeds a flow of current back to the sensor 10 to reduce the load on the reference electrode 46. The electrode 42 again is positioned in the opening 36, and is in the form generally of a flat wire mesh electrode. The chloride ions from electrolyte 20 migrate to the electrode 42 across the anion exchange membrane 40. A suitable membrane 40 is comprised of a poly(vinyl benzene) backbone with pendent quaternary ammonium groups, and is commercially available under the designation 103QZL-386 from Ionics, Inc., Watertown, Mass.

Both the cation and anion exchange membranes 24 and 40, respectively, are preferably sufficiently thick and strong enough to not be punctured or torn by the flat wire mesh electrodes 26 and 46 in use or as the sensor 10 is being assembled or re-assembled. The thin semipermeable, hydrophobic PTFE film layer 44 and the porous support 38 of the second flat ion exchange membrane assembly 16, it should be noted, serve essentially the same purposes in assembly 16 as described above with reference to the first assembly 14.

Referring now to FIG. 2, the modified amperometric sensor portion 54 of the sensor apparatus of the present invention is shown. The sensor 54 of the present invention differs from that shown in FIG. 1 and previously known to us in the use of a layer of an electrochemically inert hydrated salt or combination of such salts to provide water for the reduction of chlorine, for example, at the first, sensing electrode 26.

In the sensor 54, all of the elements may then be essentially as described above (and have been numbered accordingly), except for a modified first, flat ion-exchange membrane assembly 56 incorporating a layer 58 of an electrochemically inert hydrated salt or combination of such salts. This layer 58 is preferably positioned against and over the first electrode 26 so that any chlorine permeating through the film layer 28 must pass through the salt layer 58 before encountering the electrode 26.

The means for retaining the salt or combination of salts in this position generally comprises the semipermeable, hydrophobic film layer 28 positioned flatly against and over the salt layer 58, and held in place at its circumference by the elements 30 and 34.

The layer 58 of the inert hydrated salt or combination of such salts preferably is at least about 5 mils thick, more preferably is at least about 10 mils thick, and most preferably is at least about 15 mils thick so that the apparatus retains a substantial degree of ambient humidity-independence over at least about 6 months with a minimum of maintenance and without recalibration. Further, the sensor apparatus of the present invention should by virtue of the layer 58 be useful in fluid environments having low water contents, for example, at water contents corresponding to a relative humidity of about 40 percent or less, especially about 20 percent or less, and most especially about 10 percent or less at temperatures in the range of from about 20 to about 30 degrees Celsius.

A "substantial degree of ambient-humidity independence" in this regard means that the sensor apparatus should show, at a constant chlorine concentration, an essentially flat response to changes of a given magnitude in the water content of the surrounding fluid environment.

Preferably, at a chlorine concentration of about 5 to about 10 parts per million, the response of the sensor apparatus of the present invention should not change by more than about 1 percent given a 5 percent change in the relative humidity of the surrounding fluid environment for temperatures in the range of from about 20 to about 30 degrees Celsius. More preferably, the response will not change by a greater amount even for changes of about 50 percent in the relative humidity of the surrounding fluid environment when at such temperatures.

In terms of the effectiveness of the sensor apparatus of the present invention in fluid environments having low water contents, it is considered that the present sensor apparatus should show an essentially linear response at the particular water content as the chlorine concentration in the environment changes over the range of from about 0.1 to about 4000 parts per million, especially from about 0.1 to about 100 parts per million, and most particularly from about 0.1 to about 10 parts per million.

A preferred method of constructing the layer 58 would involve placing the equivalent of about 0.1 grams of an electrochemically inert hydrated salt (or a combination of such salts) over a first electrode 26 covering an area of about 0.05 square inches, adding a small amount (e.g., about 0.1 to 0.2 milliliters) of a saturated aqueous solution of the salt to the hydrated salt so that the particle sizes of the hydrated salt are reduced and so that the salt is spread more evenly over the surface of the first electrode 26, and then carefully removing via a paper tissue as much of the added and excess water as possible without damaging the salt layer 58.

By spreading the salt(s) more effectively over the area of the electrode 26 and by reducing the particle sizes of the salt(s), incoming chlorine molecules are more effectively intercepted and any tendency of the sprinkled hydrated salt layer 58 to cause the formation of an adjacent, thick layer of water is controlled with a minimum of water buildup. Removing any excess water improves the transmission into the layer 58 of incoming chlorine or the like.

The electrochemically inert hydrated salt(s) preferably comprise lithium sulfate ($Li_2SO_4 \cdot 2H_2O$). Other hydrated salts which could be used include, for example, lithium tartrate ($Li_2C_4H_4O_6 \cdot 6H_2O$) and lithium citrate ($Li_2C_6H_5O_7 \cdot 4H_2O$).

Further improvements in the insensitivity of the present inventive apparatus to changes in the water content of the sensor's fluid environment, and in the effectiveness of the sensor apparatus in low water content environments may be had by preconditioning the membrane 24.

A preferred method of preconditioning the membrane 24 would be as described in commonly-assigned U.S. Pat. No. 4,724,050 to Bergeron et al., with such patent being incorporated herein by reference.

In brief, in the referenced patent to Bergeron et al., a method is described for electrolytically pretreating a cation exchange membrane which comprises two steps. In a first step, a cation exchange membrane is used to partition a first aqueous electrolyte solution from a second aqueous electrolyte solution. The first solution is disclosed as having a cation composition in which hydrogen ion and a single cation moiety selected from the group consisting of alkali metal cations and alkali earth metal cations (e.g., lithium cations) constitute more than 99.99% of the composition, and the second solution is preferably the same. An electrical current is then sequentially passed through the first electrolytic solution, the membrane to be treated, and the second electrolytic solution. This process is said to result in converting the membrane to the cation (lithium) form of the first electrolytic solution, and in the removal from the membrane of unwanted and interfering trace level impurity cations, such as cations of transition metals.

The present sensor apparatus can be used in several ways, for example as a perimeter monitor for chlorine or as a monitor for chlorine in a process stream (or a slip stream from a process stream, as in a flow cell), especially a process stream which is substantially anhydrous. The apparatus may preferably also be employed with any suitable, known calibration means for releasing a known quantity of the oxidizing or reducing agent species into the fluid environment of the sensor, whereupon a resulting flow of electrical current may be used to gauge subsequent encounters with unknown concentrations of the oxidizing or reducing agent species. When used as a perimeter monitor or as a process monitor where large chlorine concentrations are unlikely to be encountered, a conventional loop-powered arrangement may be employed for placing the apparatus in service.

Where, as in certain process applications, there is a risk of large chlorine concentrations being encountered by the sensor apparatus, then preferably the electronic portion of the sensor apparatus will be as generally shown in FIG. 3. A particularized discussion of circuit elements suited to the performance of each of the functions shown schematically in FIG. 3 will not be undertaken herein, however, in that those skilled in the art will be well able to select and arrange these elements so as to accomplish these functions.

Referring now to FIG. 3, an applied voltage generator 60 provides a setpoint voltage for a current booster amplifier 62. The current booster amplifier 62 drives current through the three-electrode cell via the third, driven electrode 42 to produce a controlled potential between the reference electrode 46 and the first, sensing electrode 26. The reference electrode potential provides a feedback loop to adjust the drive current to maintain this controlled potential. Impedance of the reference electrode circuit (through the electrometer 64) is high so as to minimize current flow through the reference electrode 46, thereby minimizing also erosion of the reference electrode 46 in the presence of significant chlorine concentrations. Continuous current flow through the cell minimizes secondary electrochemical reactions at the sensing electrode 26, thereby maintaining a uniform sensing electrode surface.

Where gaseous chlorine is reduced to chloride ions, for example, at the first, sensing electrode 26, current flows through the cell to maintain the controlled potential between the reference and sensing electrodes 46 and 26, respectively. This current is proportional to the concentration of chlorine encountered by the sensing electrode 26 in the fluid environment surrounding the sensor 54, and is converted to voltage for further processing by means 66 for accomplishing such a conversion. Display and recorder amplifiers 68 may, for example, after zero-adjusting (offset voltage compensation) for the current continuously pushed through the cell in the absence of chlorine, display and record the measured voltage attributable to detected chlorine or more preferably will display and record directly in concentration terms (e.g., parts per million of chlorine).

The present invention is further illustrated by the following examples:

EXAMPLE 1

In this example, a chlorine sensor was constructed which employed a preconditioned Nafion ™ 324 cation exchange membrane (E. I. DuPont de Nemours & Co., Inc., 8 mils thick, 0.5 inches in diameter) and a gel of lithium chloride and water which is commercially available as "EpH" gel from Innovative Sensors, Inc., Anaheim, Calif. A silver anode was immersed in the electrolyte, while a platinum wire mesh cathode (10 mm in diameter, 15 mesh) was positioned between a Teflon ™ film (soft-compressible type C-80, 50 mils thick, 80 percent porosity, 5 micron size pores) and the preconditioned Nafion ™ membrane. The sensor did not, however, include a layer of an electrochemically inert, hydrated salt between the hydrophobic Teflon ™ PTFE film layer and the first electrode.

The membrane had been preconditioned by immersion for one hour in a boiling, lithium chloride-saturated mixture of equal parts by weight of glycerine and water.

The sensor was then placed in a dry (0 percent $H_2O$) nitrogen stream flowing at 2.5 liters per minute at ambient temperature, about 25 degrees Celsius. Chlorine gas at 5 parts per million by weight was released upstream and the sensor response was observed to drift continuously lower.

EXAMPLES 2-6

In this example, the response of the sensor apparatus of Example 1 was measured at various chlorine concentrations and relative humidities. The results of these measurements are reported in Table 1 below.

TABLE 1

| R.H. (Pct.) | 0 ppm Cl$_2$ | 3.9 ppm Cl$_2$ | 4.9 ppm Cl$_2$ | 8.0 ppm Cl$_2$ | 13.4 ppm Cl$_2$ |
| --- | --- | --- | --- | --- | --- |
| 0 | 0 | 0 | 0 | 0 | 0 |
| 10 | 0 | 0.15 | 0.2 | 0.25 | 0.50 |
| 50 | 0 | 0.4 | 0.50 | 0.8 | 1.1 |
| 100 | 0 | 0.5 | 0.8 | 1.2 | 1.7 |

The chlorine concentrations were created and maintained using a Dynacalibrator TM permeation device (from VICI Metronics, Santa Clara, CA) at several temperatures, while the relative humidities were manufactured from metered 100 percent relative humidity air and dry nitrogen.

The data in Table 1 indicate a sensitivity to relative humidity and water content in the sensor's response.

EXAMPLES 7-11

For this example, the sensor of Examples 1 and 2 was modified in accordance with the teachings of the present disclosure, by applying a 15 mil thick layer of lithium sulfate solution (molarity of 1, monohydrate) in between the platinum wire mesh electrode and the Teflon TM protective hydrophobic film layer and removing the excess water with a paper tissue.

The modified sensor was tested for its response to various concentrations of chlorine at various relative humidities, using a 1 megohm resistor in parallel combination with a voltmeter, instead of the 100 K ohm resistor used in Examples 1 and 2.

TABLE 2

| R.H. (Pct.) | 0 ppm Cl$_2$ | 3.9 ppm Cl$_2$ | 4.9 ppm Cl$_2$ | 8.0 ppm Cl$_2$ | 13.4 ppm Cl$_2$ |
| --- | --- | --- | --- | --- | --- |
| 0 | 0 | 1.1 | 1.6 | 2.4 | 3.8 |
| 10 | 0 | 1.15 | 1.55 | 2.2 | 3.65 |
| 50 | 0 | 1.2 | 1.6 | 2.2 | 3.55 |
| 100 | 0 | 1.5 | 1.7 | 2.7 | 3.9 |

Table 2 shows a lessened influence of relative humidity and changes in relative humidity and water content on the modified sensor of this example, as compared to the sensor in Examples 1 and 2.

EXAMPLES 12 AND 13

A modified chlorine sensor was constructed for this example in the manner of Examples 7-11, except that a 15 mil-thick layer of saturated lithium sulfate solution (aqueous) was applied. The excess water was again removed with a paper tissue.

The sensor's responses to a large range of chlorine concentrations at both 0 percent relative humidity and 100 percent relative humidity were studied for comparison, and are reported below in Table 3. The chlorine concentrations were generated by a device described in commonly-assigned U. S. Ser. No. 07/300,466, filed Jan. 23, 1989.

TABLE 3

| R.H. (Pct.) | 0 ppm Cl$_2$ | 100 ppm Cl$_2$ | 250 ppm Cl$_2$ | 500 ppm Cl$_2$ | 750 ppm Cl$_2$ | 1000 ppm Cl$_2$ |
| --- | --- | --- | --- | --- | --- | --- |
| 0 | 0 | 1.1 | 3.3 | 7.7 | 11.6 | 13.0 |
| 100 | 0 | 1.6 | 4.0 | 9.3 | 12.0 | 13.0 |

The data from Table 3 show the impact of environmental water on the sensor's response over a larger range of chlorine concentrations than in Table 2, and suggest again a lessened degree of dependence compared to an unmodified sensor.

EXAMPLE 14

The sensor of Examples 12 and 13 was tested in this example in an anhydrous gaseous environment with a constant chlorine concentration of 4.9 parts per million, using a conventional voltmeter and a one million ohm resistor in parallel combination. The sensor's response to this concentration over time was studied as a measure of the sensor's longevity of response, in milliamps from a baseline at 0 parts per million chlorine concentration.

The actual measurements taken are shown below in Table 4. These measurements show a decline of about 2 percent or less in the sensor's response after about 10 hours in the anhydrous environment. A decline of about 3.6 percent overall is seen after about 15 hours, while a decline of about 4.3 percent is seen after about 20 hours.

TABLE 4

| Time (Hrs.) | Response (milliamps) |
| --- | --- |
| 0 | 5.60 |
| 1 | 5.60 |
| 10 | 5.50 |
| 15 | 5.45 |
| 20 | 5.40 |

While preferred embodiments and illustrative examples of the apparatus of the present invention have been described and provided herein, those skilled in the art will readily appreciate that various changes may be made therein without departing in scope or spirit from the present invention as more particularly defined by the claims below. For example, while a three-wire embodiment including a layer of an electrochemically-inert hydrated salt or combination of such salts is preferred, the benefits of employing the salt layer can be realized in a two-wire version as well.

What is claimed is:

1. A sensor suited for use in an apparatus for the quantitative determination of chemical oxidizing or reducing agents in a fluid environment, comprising:
   a first, sensing electrode for contacting oxidizing or reducing agents in the fluid environment and producing an ionic species therefrom;
   a layer of an electrochemically inert hydrated salt or combination of electrochemically inert hydrated salts adjacent the first electrode and through which an oxidizing or reducing agent species must pass to encounter the first electrode;
   means for retaining the layer of salt(s) in such position;
   a reservoir of an electrolytic solution;
   a second electrode in contact with the reservoir of electrolytic solution; and
   an ion-exchange membrane separating the electrolytic solution and second electrode from the first electrode, which prevents the ionic species produced at the first electrode from an oxidizing or reducing agent from passing into the reservoir of electrolytic solution.

2. A sensor as defined in claim 1, wherein the fluid environment has a water content corresponding to a relative humidity of about 40 percent or less at temperatures in the range of from about 20 to about 30 degrees Celsius, and wherein when the sensor is used as part of an apparatus for the quantitative determination of chemical oxidizing or reducing agents in such a fluid environment, the response of the apparatus is essentially linear for concentrations of an oxidizing or reducing agent species ranging from about 0.1 to about 4000 parts per million.

3. A sensor as defined in claim 2, wherein the response of the apparatus is essentially linear for concentrations of an oxidizing or reducing agent species ranging from about 0.1 to about 100 parts per million.

4. A sensor as defined in claim 3, wherein the response of the apparatus is essentially linear for concentrations of an oxidizing or reducing agent species ranging from about 0.1 to about 10 parts per million.

5. A sensor as defined in claim 1, wherein the fluid environment has a water content corresponding to a relative humidity of about 20 percent or less at temperatures in the range of from about 20 to about 30 degrees Celsius, and wherein when the sensor is used as part of an apparatus for the quantitative determination of chemical oxidizing or reducing agents in such a fluid environment, the response of the apparatus is essentially linear for concentrations of an oxidizing or reducing agent species ranging from about 0.1 to about 4000 parts per million.

6. A sensor as defined in claim 5, wherein the response of the apparatus is essentially linear for concentrations of an oxidizing or reducing agent species ranging from about 0.1 to about 100 parts per million.

7. A sensor as defined in claim 6, wherein the response of the apparatus is essentially linear for concentrations of an oxidizing or reducing agent species ranging from about 0.1 to about 10 parts per million.

8. A sensor as defined in claim 1, wherein the fluid environment has a water content corresponding to a relative humidity of about 10 percent or less at temperatures in the range of from about 20 to about 30 degrees Celsius, and wherein when the sensor is used as part of an apparatus for the quantitative determination of chemical oxidizing or reducing agents in such a fluid environment, the response of the apparatus is essentially linear for concentrations of an oxidizing or reducing agent species ranging from about 0.1 to about 4000 parts per million.

9. A sensor as defined in claim 8, wherein the response of the apparatus is essentially linear for concentrations of an oxidizing or reducing agent species ranging from about 0.1 to about 100 parts per million.

10. A sensor as defined in claim 9, wherein the response of the apparatus is essentially linear for concentrations of an oxidizing or reducing agent species ranging from about 0.1 to about 10 parts per million.

11. A sensor as defined in claim 1, wherein at a chlorine concentration in the fluid environment in the range of from about 5 to about 10 parts per million, the sensor when used as part of an apparatus for the quantitative determination of chlorine in a fluid environment demonstrates a change in response of no more than about 1 percent when the water content of the fluid environment changes to an extent corresponding to a 5 percent change in relative humidity at temperatures in the range of from about 20 to about 30 degrees Celsius.

12. A sensor as defined in claim 11, wherein at a chlorine concentration in the fluid environment in the range of from about 5 to about 10 parts per million, the sensor when used as part of an apparatus for the quantitative determination of chlorine in a fluid environment demonstrates a change in response of no more than about 1 percent when the water content of the fluid environment changes to an extent corresponding to a 50 percent change in relative humidity at temperatures in the range of from about 20 to about 30 degrees Celsius.

13. A sensor as defined in claim 1, wherein the ion-exchange membrane has been preconditioned by placing the membrane in an electrolyte solution of hydrogen ion and a single cation moiety selected from the group consisting of alkali metal cations and alkali earth metal cations, and then passing an electrical current through the electrolyte solution and membrane.

14. A sensor as defined in claim 1, wherein the electrolytic solution is in the form of a gel.

15. A sensor as defined in claim 1, wherein the first electrode is in the form of a flat wire mesh positioned against the ion-exchange membrane, with the layer of hydrated salt(s) on an opposite side of the flat wire mesh first electrode from the ion-exchange membrane.

16. A sensor as defined in claim 15, wherein the sensor further comprises a protective semipermeable, hydrophobic film layer on a side of the layer of hydrated salt(s) opposite the first wire mesh electrode which permits water vapor and the oxidizing or reducing agent species to pass therethrough.

17. A sensor suited for use in a apparatus for the quantitative determination of chemical oxidizing or reducing agents in a fluid environment, comprising:
a first, sensing electrode for contacting oxidizing or reducing agents in a fluid environment and producing an ionic species therefrom;
a reservoir of an electrolytic solution;
a second, reference electrode in contact with the reservoir of electrolytic solution;
a layer of an electrochemically inert hydrated salt or salts positioned adjacent the first electrode and through which an oxidizing or reducing agent species must pass to encounter the first electrode;
means for retaining the layer of salt(s) in such position;
a third, externally-driven electrode which in operation is in contact with the fluid environment and which supplies current to the sensing electrode that would otherwise be supplied by the corrosion in the electrolytic solution of the second electrode;
a first ion-exchange membrane separating the electrolytic solution and second electrode from the first electrode, which prevents the ionic species produced at the first electrode from an oxidizing or reducing agent from passing into the reservoir of electrolytic solution; and
a second ion-exchange membrane separating the electrolytic solution and second electrode from the third electrode, wherein the second ion-exchange membrane admits passage of oppositely-charged ionic species from those admitted by the first ion-exchange membrane.

18. An apparatus for the quantitative determination of chemical oxidizing or reducing agents in a fluid environment, comprising:
a sensor which includes:
a first, sensing electrode for contacting oxidizing or reducing agents in the fluid environment and producing an ionic species therefrom;
a layer of an electrochemically inert hydrated salt or combination of electrochemically inert hydrated salts adjacent the first electrode and through which an oxidizing or reducing agent species must pass to encounter the first electrode;

means for retaining the layer of salt(s) in such position;

a reservoir of an electrolytic solution;

a second electrode in contact with the reservoir of electrolytic solution; and an ion-exchange membrane separating the electrolytic solution and second electrode from the first electrode, which prevents the ionic species produced at the first electrode from an oxidizing or reducing agent from passing into the reservoir of electrolytic solution;

means for placing the first and second electrodes in electrical contact; and means for measuring a flow of electrical current generated between the electrodes.

19. An apparatus for the quantitative determination of chemical oxidizing or reducing agents in a fluid environment, comprising:

a sensor which includes:

a first, sensing electrode for contacting oxidizing or reducing agents in a fluid environment and producing an ionic species therefrom;

a reservoir of an electrolytic solution;

a second, reference electrode in contact with the reservoir of electrolytic solution;

a layer of an electrochemically inert hydrated salt or salts positioned adjacent the first electrode and through which an oxidizing or reducing agent species must pass to encounter the first electrode;

means for retaining the layer of salt(s) in such position;

a third, externally-driven electrode which in operation is in contact with the fluid environment and which supplies current to the sensing electrode that would otherwise be supplied by the corrosion in the electrolytic solution of the second electrode;

a first ion-exchange membrane separating the electrolytic solution and second electrode from the first electrode, which prevents the ionic species produced at the first electrode from an oxidizing or reducing agent from passing into the reservoir of electrolytic solution; and a second ion-exchange membrane separating the electrolytic solution and second electrode from the third electrode, wherein the second ion-exchange membrane admits passage of oppositely-charged ionic species from those admitted by the first ion-exchange membrane;

an applied voltage generator;

a current booster amplifier for driving current through the sensor via the third electrode to produce a controlled potential between the first and second electrodes;

a feedback loop to adjust the drive current through the third electrode so as to maintain the controlled potential, said feedback loop offering high impedance to current flow through the reference electrode;

a current to voltage convertor converting current flow through the sensor to voltage; and means for zero-adjusting the converted voltage to offset the voltage attributable to the current produced via said applied voltage generator.

20. A chlorine sensor suited for use in an apparatus for the quantitative determination of chlorine in a fluid environment, comprising:

a first, platinum flat wire mesh sensing electrode for contacting chlorine in the fluid environment and reducing chlorine to chloride ions;

a layer of an electrochemically inert hydrated lithium salt or combination of electrochemically inert hydrated lithium salts adjacent the first electrode and through which the chlorine must pass to encounter the first electrode;

a protective semipermeable, hydrophobic film layer positioned against the layer of salt(s) for holding the layer of salt(s) in such position;

a reservoir of a gelatinous electrolytic solution of lithium chloride and water;

a second, silver electrode in contact with the reservoir of electrolytic solution; and a cation ion-exchange membrane separating the electrolytic solution and second electrode from the first electrode.

21. A chlorine sensor suited for use in an apparatus for the quantitative determination of chlorine in a fluid environment, comprising:

a first, platinum flat wire mesh sensing electrode for contacting the chlorine in the fluid environment and reducing chlorine to chloride ions;

a reservoir of a gelatinous electrolytic solution of lithium chloride and water;

a second, silver reference electrode in contact with the reservoir of electrolytic solution;

a layer of an electrochemically inert hydrated lithium salt or lithium salts positioned adjacent the first electrode and through which chlorine must pass to encounter the first electrode;

a protective semipermeable, hydrophobic film layer positioned against the layer of salt(s) for holding the layer of salt(s) in such position;

a third, externally-driven platinum flat wire mesh electrode which in operation is in contact with the fluid environment and which supplies current to the sensing electrode that would otherwise be supplied by the corrosion in the electrolytic solution of the second electrode;

a cation ion-exchange membrane separating the electrolytic solution and second electrode from the first electrode;

an anion ion-exchange membrane separating the electrolytic solution and second electrode from the third electrode; and a protective semipermeable, hydrophobic film layer positioned over the third electrode.

22. An apparatus for the quantitative determination of chlorine in a fluid environment, comprising:

a sensor which includes:

a first, platinum flat wire mesh sensing electrode for contacting chlorine in the fluid environment and reducing chlorine to chloride ions;

a layer of an electrochemically inert hydrated lithium salt or combination of electrochemically inert hydrated lithium salts adjacent the first electrode and through which the chlorine must pass to encounter the first electrode;

a protective semipermeable, hydrophobic film layer positioned against the layer of salt(s) for holding the layer of salt(s) in such position;

a reservoir of a gelatinous electrolytic solution of lithium chloride and water;

a second, silver electrode in contact with the reservoir of electrolytic solution; and a cation ion-exchange membrane separating the electrolytic solution and second electrode from the first electrode;

means for placing the first and second electrodes in electrical contact; and means for measuring a flow of electrical current generated between the electrodes.

23. An apparatus for the quantitative determination of chlorine in a fluid environment, comprising:

a sensor which includes:

a first, platinum flat wire mesh sensing electrode for contacting the chlorine in the fluid environment and reducing chlorine to chloride ions;

a reservoir of a gelatinous electrolytic solution of lithium chloride and water;

a second, silver reference electrode in contact with the reservoir of electrolytic solution;

a layer of an electrochemically inert hydrated lithium salt or lithium salts positioned adjacent the first electrode and through which chlorine must pass to encounter the first electrode;

a protective semipermeable, hydrophobic film layer positioned against the layer of salt(s) for holding the layer of salt(s) in such position;

a third, externally-driven platinum flat wire mesh electrode which in operation is in contact with the fluid environment and which supplies current to the sensing electrode that would otherwise be supplied by the corrosion in the electrolytic solution of the second electrode;

a cation ion-exchange membrane separating the electrolytic solution and second electrode from the first electrode;

an anion ion-exchange membrane separating the electrolytic solution and second electrode from the third electrode; and a protective semipermeable, hydrophobic film layer positioned over the third electrode;

an applied voltage generator;

a current booster amplifier for driving current through the sensor via the third electrode to produce a controlled potential between the first and second electrodes;

a feedback loop to adjust the drive current through the third electrode so as to maintain the controlled potential, said feedback loop offering high impedance to current flow through the reference electrode;

a current to voltage convertor converting current flow through the sensor to voltage; and means for zero-adjusting the converted voltage to offset the voltage attributable to the current produced via said applied voltage generator.

* * * * *